United States Patent
Kranz

(10) Patent No.: US 6,197,047 B1
(45) Date of Patent: Mar. 6, 2001

(54) STENT

(75) Inventor: Curt Kranz, Berlin (DE)

(73) Assignee: Biotronik Mess- und Therapiegeräte GmbH & Co. Ingenieurburo Berlin, Berlin (DE)

( * ) Notice: Subject to any disclaimer, the term of this patent is extended or adjusted under 35 U.S.C. 154(b) by 0 days.

(21) Appl. No.: 09/083,156

(22) Filed: May 22, 1998

(30) Foreign Application Priority Data

May 23, 1997 (DE) .............................................. 197 22 857

(51) Int. Cl.[7] .......................................................... A61F 2/06
(52) U.S. Cl. .............................................. 623/1.15; 623/1.1
(58) Field of Search .................................... 623/1, 12, 1.1, 623/1.15, 1.16, 1.18, 1.2; 606/198, 195

(56) References Cited

U.S. PATENT DOCUMENTS

| | | |
|---|---|---|
| 5,197,978 | 3/1993 | Hess . |
| 5,545,210 * | 8/1996 | Hess et al. ................................. 623/1 |
| 5,556,413 * | 9/1996 | Lam ...................................... 6/198 X |
| 5,591,197 * | 1/1997 | Orth et al. ................................. 623/1 |
| 5,755,781 * | 5/1998 | Jayaraman ................................. 623/1 |
| 5,849,206 * | 12/1998 | Amon et al. ............................ 216/63 |
| 5,922,021 * | 7/1999 | Jang ........................................ 623/1 |

FOREIGN PATENT DOCUMENTS

| | | |
|---|---|---|
| 43 03 181 | 8/1994 | (DE) . |
| 19540 851 | 5/1997 | (DE) . |
| 0 335 341 | 10/1989 | (EP) . |
| 0 364 787 | 4/1992 | (EP) . |
| WO 96 29028 | 9/1926 | (WO) . |
| WO9603092 | 2/1996 | (WO) . |

* cited by examiner

Primary Examiner—Michael J. Milano
Assistant Examiner—Hieu Phan
(74) Attorney, Agent, or Firm—Venable; Robert Kinberg; Catherine Voorhees

(57) ABSTRACT

A stent, particularly a coronary stent, which includes at least one thin-walled, tubular body (2), the surface (1) of which is divided into strap-like, expandable elements (4,4',4",4''', 4"") extending in the longitudinal direction of the stent and expandable in the circumferential direction thereof and, which elements are linked by at least one joining strap (6,6'). Two expandable elements (4,4',4",4''',4"") are juxtaposed in the circumferential direction of the stent and, by means of an end attachment (8), with the end face (4.4') of an expandable element (4,4',4",4''',4"") adjoining in the longitudinal direction of the stent. The surface (1) in the non-expanded condition is substantially free of apertures and is divided by partition lines (3), which have a considerably smaller width compared with the strap width of the expandable elements (4,4',4",4''',4"").

33 Claims, 7 Drawing Sheets

STENT

BACKGROUND OF THE INVENTION

The invention relates to a stent, particularly a coronary stent, as an intraluminal expansion element, and a method of manufacturing the stent.

An expandable intraluminal element with at least one thin-walled, tubular part (hereinafter referred to as a stent) is known from European patent specifications EP 0 364 787 B1 and EP 335 341 B1. The surface of the stent is made of net-like open work and contains apertures, which are bounded by strap-like elements of low material thickness extending in straight lines in the longitudinal axial and circumferential directions. The strap-like elements, which can expand in the circumferential direction of the stent, comprise the remains of the tubular wall from which the material in the area of the apertures has been removed.

Another tubular stent, also of net-like structure, is known from international patent application WO 96 03 092 A1. The stent is made up of straps in a meander-shaped arrangement, extending partly in the circumferential and partly in the longitudinal axial direction of the stent. The surface of the stent is similarly made of open-work and has apertures between the straps, in the area of which the material has been removed from the tubular wall.

Stents of this type are expanded during an operation, with outwardly directed forces exerted by a tubular dilator to which high-pressure gas is applied. The stent retains its tubular shape in spite of the deformation, and expands the vessel narrowed by deposits.

For safety reasons deformation of the straps is kept far below a possible danger level, as breakage of a strap would cause its free ends in the region of the breakage to project into the interior of the vessel fitted with the stent. The accompanying risk of the formation of restenosis would not only put the success of the actual operation into question but also endanger the life of the patient.

Thin net structures of the known stent are very susceptible to mechanical damage by exertion of a force, during the period from manufacture to use, and this damage may make them useless of even dangerous. Such damage may not be detected in the non-expanded state and could lead to the final breakage of one or more straps only when the stent is expanded, with the detrimental effects described above.

Known stents also have the drawback that production of their net-like structure is very time-consuming and requires a large outlay on removal of the material cut out of the surface to create the apertures.

SUMMARY OF THE INVENTION

In view of the defects of the state of the art, the invention is based on the problem of providing an expandable stent of the above-mentioned type which is simple to produce and has good stability even in the non-expanded condition, and providing a method of manufacturing the stent.

The problem is solved by a stent with the features of.

The invention includes the technical teaching that, in a stent of the above type, both production costs and susceptibility to damage can be greatly reduced if the surface of the initial tubular body in the non-expanded condition of the stent is substantially free of apertures and is divided into expandable elements which are linked by narrow partition lines.

This teaching has the advantage of considerably reducing the cutting cost because fewer and shorter cuts have to be made in the surface in order to form the dividing partition lines. Secondly far less material has to be taken out in manufacture, thereby reducing both the expenditure on removing the material and the amount of waste to be disposed of.

A further advantage is that the stent surface, which is substantially free of apertures in the non-expanded condition, is far less susceptible to mechanical damage than the previous net-like stents, as forces are directed into the stent structure over a wide area and not concentrated on thin individual components of a net-like structure. Damage to the stent through mechanical strains in production, storage, transportation or even before and during the operation is therefore far more improbable.

Another advantage of the stent according to the invention is that in the expanded condition it covers a considerably larger part of the wall of the vessel than known stents of net-like structure do. The area of the vessel wall which is available for fresh deposits is thereby appreciably reduced, so that the risk of restenosis forming is further diminished.

The feature of the invention that the surface is substantially free of apertures should be understood as meaning that a substantial proportion of the surface has a closed surface, divided only by partition lines. Quite small openings may however be provided, e.g., inside the individual expandable elements, if the total area of the small openings is not significant relative to the surface.

In a preferred embodiment of a stent according to the invention the partition lines are of a width substantially corresponding to that of a clean incision when the surface is severed by means of a cutting beam, e.g. a cutting jet of water preferably a laser beam. Narrow partition lines give the non-expanded stent particularly high stability.

The partition lines are therefore preferably of a width substantially corresponding to the minimum obtainable width of a clean incision when the surface is severed by means of a cutting beam, particularly a laser beam. This not only gives the stent high stability, due to the narrow width of the partition lines, but the production time for the stent may also be shortened, as the width of a clean incision is directly related to the speed at which the cutting beam advances. The minimal partition line width is obtained precisely at the maximum advancing speed of the cutting beam and at which a clean incision is still produced in the severing of the surface by means of the beam.

In another preferred embodiment of the stent according to the invention, the joining straps are inclined to both the longitudinal and the circumferential directions of the stent and are laterally defined substantially over their whole length, between adjacent expandable elements, by the respective partition line defining the external contour of the respective expandable element in that region. The effect of this arrangement, obtained in a simple manner, is that no gaps, i.e. apertures, are formed between the longitudinal sides of the individual expandable elements, and a second effect is that a single partition line defines both part of the contour of the expandable element and half the external contour of the link strap to the adjoining expandable element, so that manufacturing costs are reduced.

An advantage of the stent according to the invention the external contour of the expandable elements is symmetrical with their longitudinal axis. Each element may have a flat first section extending in both the longitudinal and the circumferential direction, and a second section extending at least substantially in the circumferential direction, which sections are linked by an intermediate section extending substantially in the longitudinal direction. This formation of the expandable elements allows a particularly space-saving, tightly packed arrangement thereof, with reduced gaps between them. Thus the expandable elements may, e.g., be structured and arranged so that the second section of an element projects into the constriction formed by the intermediate section, between the first and second sections of the adjacent element, thereby minimizing space between the two elements. This further reduces any possible openings in the surface.

The individual sections, particularly the first and second ones, are preferably produced from regular shapes such as circles, ellipses, rectangles, squares, polygons or formations combining or approximating to these.

In a particularly beneficial embodiment of a stent according to the invention, pairs of expandable elements adjoining each other in the circumferential direction of the stent are turned through 180° from each other. The first section of one element goes into the gap between the first and second sections of the other element. The joining strap is further arranged between the first two sections, and the directly opposing external contours of the two elements are bounded by the same partition lines. As a result, firstly the manufacturing cost of the stent is advantageously reduced, since parts of the external contours of two adjoining elements are defined by one partition line, thus reducing the number and length of partition lines to be made. Secondly no appreciable apertures appear between the expandable elements adjoining each other in the circumferential direction of the stent, as the elements fit closely together with virtually no gaps, and the joining strap fills the gap left between the two elements. The fronts of the second sections then preferably run straight in the circumferential direction, to allow other expandable elements to be joined without any gaps in the longitudinal direction of the stent.

As a means of forming a narrow strap running round along the external contour inside the expandable elements, a further advantageous embodiment has an internal partition line running at a substantially constant distance from the external contour, at least in sections. Elements which can expand in a circumferential direction are thus formed in a particularly simple manner. The peripheral strap, with which the joining elements are linked, can be deformed in the manner of known strap-like expandable elements when the stent is expanded, and thus ensure the desired functioning of the stent. The strap is of constant width at least in sections— e.g. in the regions of the individual sections of the element— in order to ensure even distribution of the deformation over the whole strap when expansion takes place.

The internal partition line preferably runs at a substantially constant distance from the external contour in the first section, runs along the axis of symmetry in the intermediate section and is substantially T-shaped in the second section. Apertures in the stent surface are thus advantageously prevented, at least in the intermediate section and second section of the expandable elements. The cross-piece of the T-shaped partition line in the second section preferably runs substantially parallel with the end face, i.e. the side of the second section facing away from the first section, in order to ensure that the peripheral strap has adequate deformability in that region.

In a particularly beneficial version the internal partition line in the first section has an interruption, thereby creating a link between the peripheral strap and the region inside the expandable element bounded by it. This advantageously avoids the formation of an aperture inside the expandable element. The whole surface of the stent can thus be made free of apertures in a simple manner.

The interruption of the internal partition line in the first section of the expandable elements is preferably located in the region of the end face of the first section, i.e. the side facing away from the second section. Since the interruption is in the region of the axis of symmetry of the expandable element, where there is little deformation of the peripheral strap, the effect is firstly that the deformation of that strap on expansion of the stent is particularly even and symmetrical, and secondly that the link created by the interruption of the partition line is least stressed at that location.

In a preferred embodiment the respective joining strap in the part of the intermediate section adjoining the first section is linked with the expandable element and separated from the respective first section by a partition line. There is consequently a particularly favourable input of force into the peripheral strap and hence particularly favourable deformation of that strap when the stent is expanded.

In another preferred embodiment of the stent according to the invention, the attachment of the expandable element to the expandable element adjoining it longitudinally of the stent is arranged at the end face of the first section. As with the arrangement of the interruption of the internal partition line, the advantages of even deformation of the peripheral strap and little stress on the attachment are also obtained here.

In a beneficial embodiment of the stent according to the invention, the attachment includes at least one stretching element, arranged between the end faces of the first sections of two expandable elements adjoining each other longitudinally of the stent, which stretching element is formed by at least two substantially parallel partition lines running in the circumferential direction, as a substantially S-shaped stretching strap. The stretching strap enables the two expandable elements linked by the attachment to move axially towards each other. This simple method provides the advantage, firstly that any shortening of the stent in its expansion can be compensated, and secondly that the whole stent can thereby be subjected to a defined buckling in the region of those stretching elements, when the stretching elements are located on a common annular section of the stent owing to the arrangement of the expandable elements. Consequently even stenoses present in curved blood vessels can be treated successfully by expanding stents. In the non-expanded condition of the stent the stretching elements preferably run in the circumferential direction in each case, as far as the stretching elements juxtaposed in the circumferential direction, to form a closed annular region on the surface of the stent.

In favorable embodiments of the stent according to the invention, pairs of expandable elements which adjoin each other in the circumferential direction of the stent are point-symmetric with each other relative to the center point of their joining strap. This makes the stent particularly simple to produce.

As a result of the process of stretching the expandable elements in the circumferential direction of the stent, which takes place simultaneously with the expansion of the stent, and as a result of the alignment of the inclined link element in the transverse direction, unlinked groups of expandable elements are displaced relative to each other, so that this movement compensates for the shortening of the stent by stretching the expandable elements.

In advantageous embodiments of the stent according to the invention, the joining elements have an inclination basically of 45° to the circumferential direction when the stent is not expanded, as particularly favourable deformation of the expandable elements is obtained in this way.

The elements which can expand in the transverse direction then interact particularly favorably with the joining elements, if the joining elements lead into these circumferentially expandable elements at an angle of over 45°, relative to their local direction.

An especially favorable structure can be obtained not only by designing for the greatest possible strength through increasing the cross-sections of the material, but also by optimising the shape of the peripheral straps and joining regions in view of the expected loads. This is done firstly by locally minimizing the maximum tensions occurring, and secondly by controlling the necessary deformations.

The joining regions between the expandable element and the joining straps or the attachment, and deflection points for the force flux in the expandable element or in the stretching strap are preferably structured so that material tensions, including notch tension, do not exceed a predetermined value on deformation.

As a local aid to local tension-free deformations, it is also preferable to provide for the joining regions between the expandable element and the joining straps or the attachment to be shaped so as to avoid any abrupt changes in the width of the strap. This has the effect of preventing material tensions, particularly in the region of intersections or branches, from exceeding a predetermined value on deformation, including notch tension.

In advantageous embodiments of the invention, the partition lines in the joining regions between the expandable element and the joining straps or the attachment, and at deflection points for the force flux in the expandable element or in the stretching strap, may have corresponding radii of curvature or a widened end region with a corresponding opening radius, in order to reduce the notch tension sensitivity of the components at those points by the rounding effect.

Local breaking open of the stent has the disadvantage of producing free, relatively sharp-edged ends within the spatial configuration of the stent; on the one hand these may pierce the wall of the vessel, or on the other hand they may reduce the cross-section of the vessel by moving out into the path of the blood.

For these reasons, it is advantageous to round all points joining the elements which move relative to each other when the stent expands; they ensure, in a simple and also advantageous manner, that the degree of local material deformation at the points of the stent structure which are critical for the appearance of stress has a minimal value, through even distribution of the deformation work, when the stent is expanded.

A preferred stent, designed as described above, is made of tantalum as the material and has a coating of amorphous silicon carbide.

In the method of the invention for making a stent according to the invention, the partition lines in the surface of the tubular body are produced by at least one cutting beam directed onto the surface and guided along the partition lines. This method excels in its particular simplicity and the high cutting precision which can be obtained. By cutting the partition lines directly into the surface of the stent blank, the stent can be made in one operation. It does not then require any further mechanical treatment, so the risk of its being damaged once the stent structure has been made is minimized.

It is possible to use a water jet cutting process to produce the partition lines. However a laser beam is preferably used as the cutting beam, firstly because very high cutting precision can be obtained, and secondly because the mechanical strains on the stent are minimized.

In a preferred form of the method, the advancing speed of the cutting beam as it travels along the path of the partition lines between the widened end regions of the partition lines has a speed component exclusively in the direction of the path of the lines. This gives a short processing time for the stent. The advancing speed of the cutting beam preferably corresponds substantially to the maximum advancing speed of the cutting beam at which a clean incision is still obtained in the surface. Not only does this minimize the processing times for the stent, but particularly narrow partition lines are also advantageously made.

In advantageous forms of the method of manufacturing the stent, the advancing speed of the cutting beam to produce the widened end regions of the partition lines intermittently has a speed component across the path of the lines. The cutting beam preferably makes an advancing movement in a meander-shaped and/or circular or elliptical pattern or a combination thereof.

In a preferred embodiment of the method of the invention, the widened end regions of the partition lines are produced by reducing the advancing speed of the cutting beam in the vicinity of those regions. This still further reduces the cost of producing the stent, as the cutting beam need not pass through any complicated movements of the path; it merely moves more slowly, in order to remove more material than at its normal advancing speed. The slower the advancing speed of the cutting beam, the more material is removed and the greater the width or rounding radius of the widened end region. In a particularly simple version the widened end regions of the partition lines are produced by holding the cutting beam still in the appropriate cutting position.

BRIEF DESCRIPTION OF THE DRAWINGS

Other advantageous developments of the invention will now be described in detail, together with the description of preferred embodiments, with reference to the accompanying drawings in which.

DETAILED DESCRIPTION OF PREFERRED EMBODIMENTS

Figure 1:
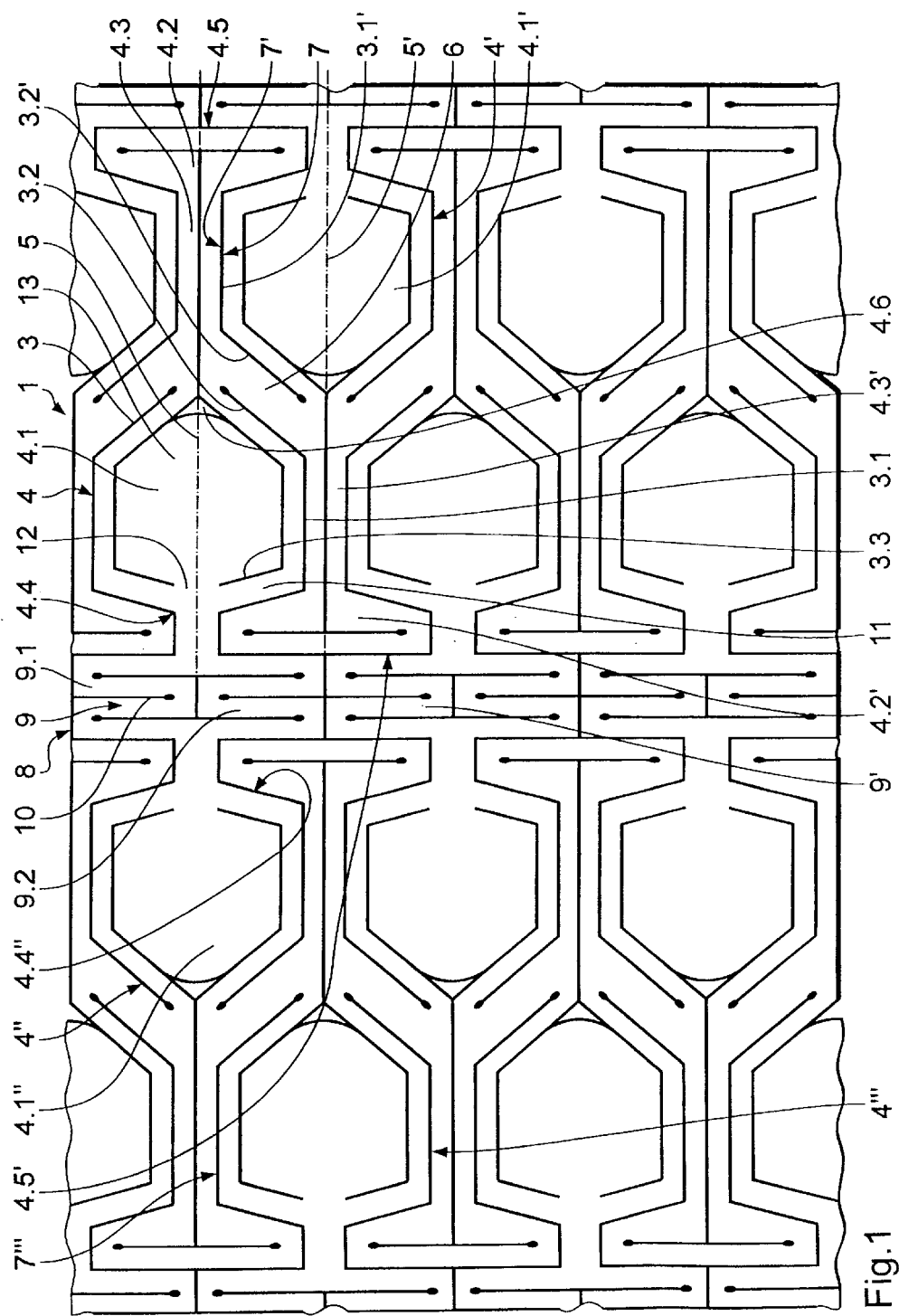
FIG. 1 shows part of a developed view of the generated surface of a non-expanded stent, as a preferred embodiment of the invention.
Figure 5:
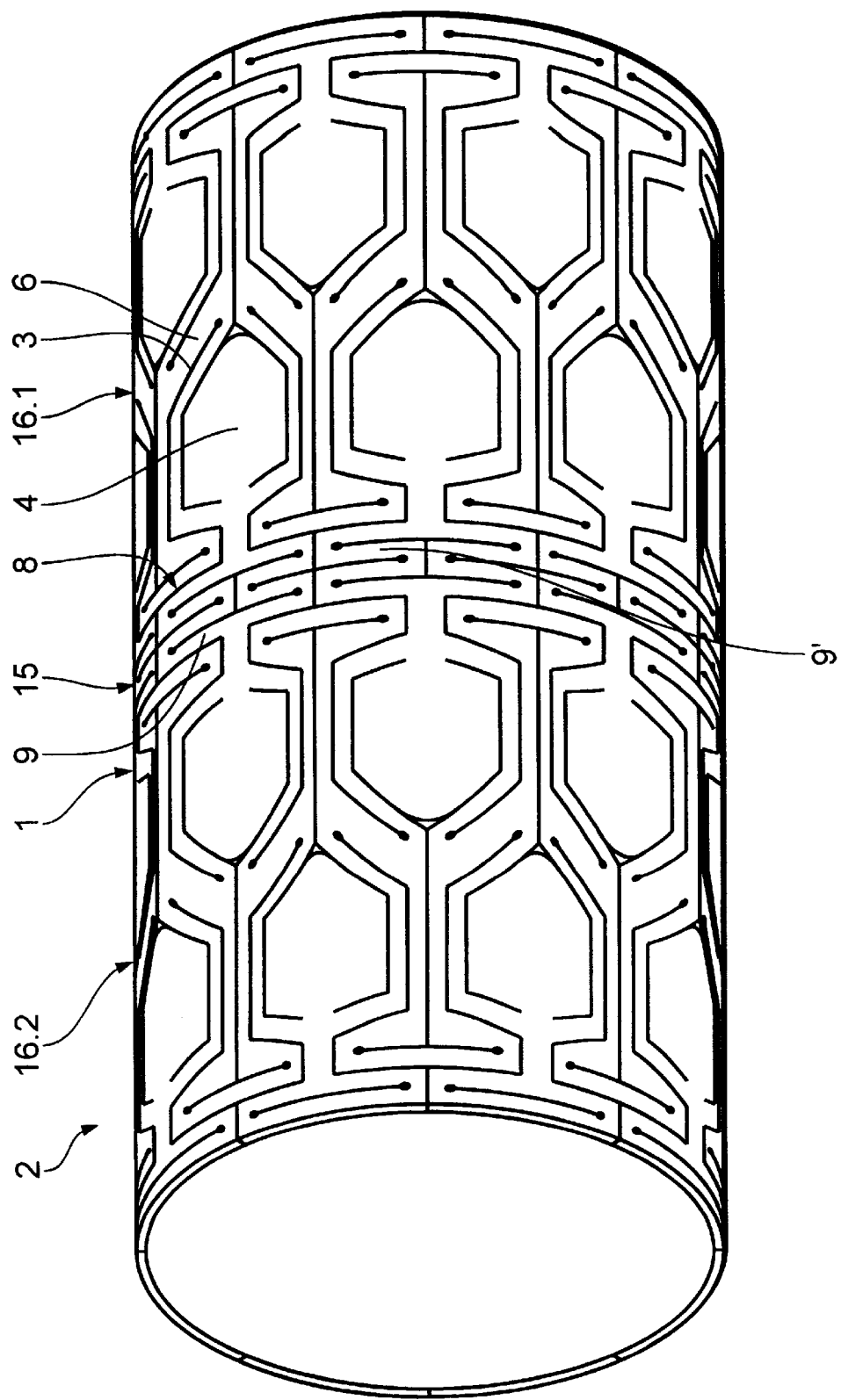
FIG. 5 is a perspective view of part of the non-developed surface according to FIG. 1, in the non-expanded condition of the stent.

FIG. 1 shows part of the developed generated surface 1 of a stent comprising a tubular body 2 (see FIG. 5). The surface 1 is divided by partition lines 3 into a plurality of similar, strap-like elements 4 extending in the longitudinal direction of the stent and expandable in its circumferential direction. The width of the partition lines 3 is considerably smaller than the strap width of the expandable elements 4. In the embodiment illustrated they have been cut into the surface 1 by a laser beam. The laser beam was taken along the path of the partition lines, advancing at the maximum speed at which a clean incision can be made in the surface 1.

The expandable elements 4 are symmetrical with their longitudinal axis 5. They have a first section 4.1 in the form of an irregular hexagon and a second section 4.2, which has the contour of an irregular pentagon and which extends substantially in the circumferential direction of the stent, i.e. at right angles to the longitudinal axis of the expandable element 4. The first section 4.1 and second section 4.2 are joined by an elongated intermediate section 4.3

Pairs of expandable elements 4, 4' which are juxtaposed in the circumferential direction of the stent are linked by a joining strap 6. The two expandable elements 4 and 4' are turned through 180° from each other, with the first section 4.1 of the first expandable element 4 fitting into the gap between the first section 4.1 and the second section 4.2' of the second expandable element 4'. In a reverse arrangement the first section 4.1' of the second expandable element 4' goes into the gap between the first section 4.1 and the second section 4.2 of the first expandable element 4. The joining strap 6 is arranged between the two first sections 4.1 and 4.1' of the two elements. It extends at an angle of approximately 45° to the circumferential direction of the stent.

The external contours 7, 7' of the expandable elements 4, 4' are formed so that the external contour regions of the two elements 4, 4' directly facing each other are bounded by the same partition lines 3.1, 3.1'. Thus the partition line 3.1 bounds both the part of the external contour 7 of the first expandable element 4, in the region where the first section 4.1 of the first expandable element 4 adjoins the second section 4.2' and the intermediate section 4.3' of the second expandable element 4', and also the second section 4.2' and intermediate section 4.3' of the second expandable element 4' itself. There is a similar arrangement with the partition line 3.1'.

The whole length of the joining strap 6 is bounded laterally by the partition lines 3.2 and 3.2', which the respective external contour 7' of the first expandable element 4 and second element 4' bounds in that region. The strap is joined to the expandable elements 4, 4' at the intermediate sections 4.3, 4.3'.

By virtue of this arrangement there are no gaps in the surface 1 of the stent between expandable elements 4, 4' juxtaposed in a circumferential direction.

An attachment 8 is arranged at the front 4.4 of the first section 4.1 of the expandable element 4, whereby the element 4 is linked to a section 4" adjoining it in the longitudinal direction of the stent. The attachment 8 includes a stretching element 9 formed into two stretching straps 9.1 and 9.2, which are in mirror image symmetrically with the longitudinal axis 5, by appropriate partition lines 10; the straps 9.1 and 9.2 substantially form a meander-shaped pattern with a double S stroke.

The external contours 7', 7'" of the expandable elements 4', 4'" are shaped in the region of the attachment 8 so that there are also no apertures between the individual components of the surface 1 in the longitudinal direction of the stent.

The stretching element 9 extends in the circumferential direction of the stent as far as the adjoining stretching elements, and the contour of the stretching elements is such that no apertures are formed in the surface 1 in a circumferential direction either.

An internal partition line 3.3, extending along the external contour 7 and formed by a narrow strap 11 running round along the external contour 7, is arranged inside the expandable element 4. In the first section 4.1 the internal partition line is substantially at a constant distance from the external contour 7; it has an interruption 12 in the region of the end face 4.4 of the first section 4.1, whereby the piece 13 of the surface bounded by the internal partition line 3.3 is joined to the strap 11 running round it. This prevents an aperture from forming in the surface 1 in the region of the piece 13. Only a negligibly small aperture 4.6 is formed in the surface 1 as a result of the rounding of the piece 13. In the region of the intermediate section 4.3 the internal partition line 3.3 runs along the longitudinal axis 5. In the second section 4.2 the internal partition line 3.3 forms a T shape, with the cross piece of the T running parallel with the end face 4.5 of the second section 4.2. This ensures that the peripheral strap 11 formed by the internal partition line 3.3 can deform evenly in the deformation during the expansion of the stent in the region of the end face 4.5, thereby reducing the tensions which occur at the end points of the internal partition line 3.3 during the deformation.

The interruption 12 is clearly not absolutely necessary in view of the otherwise completely closed surface 1, that is to say, apertures of this or other types and of substantially negligible size would be quite tolerable in the framework of the invention.

Figure 2:
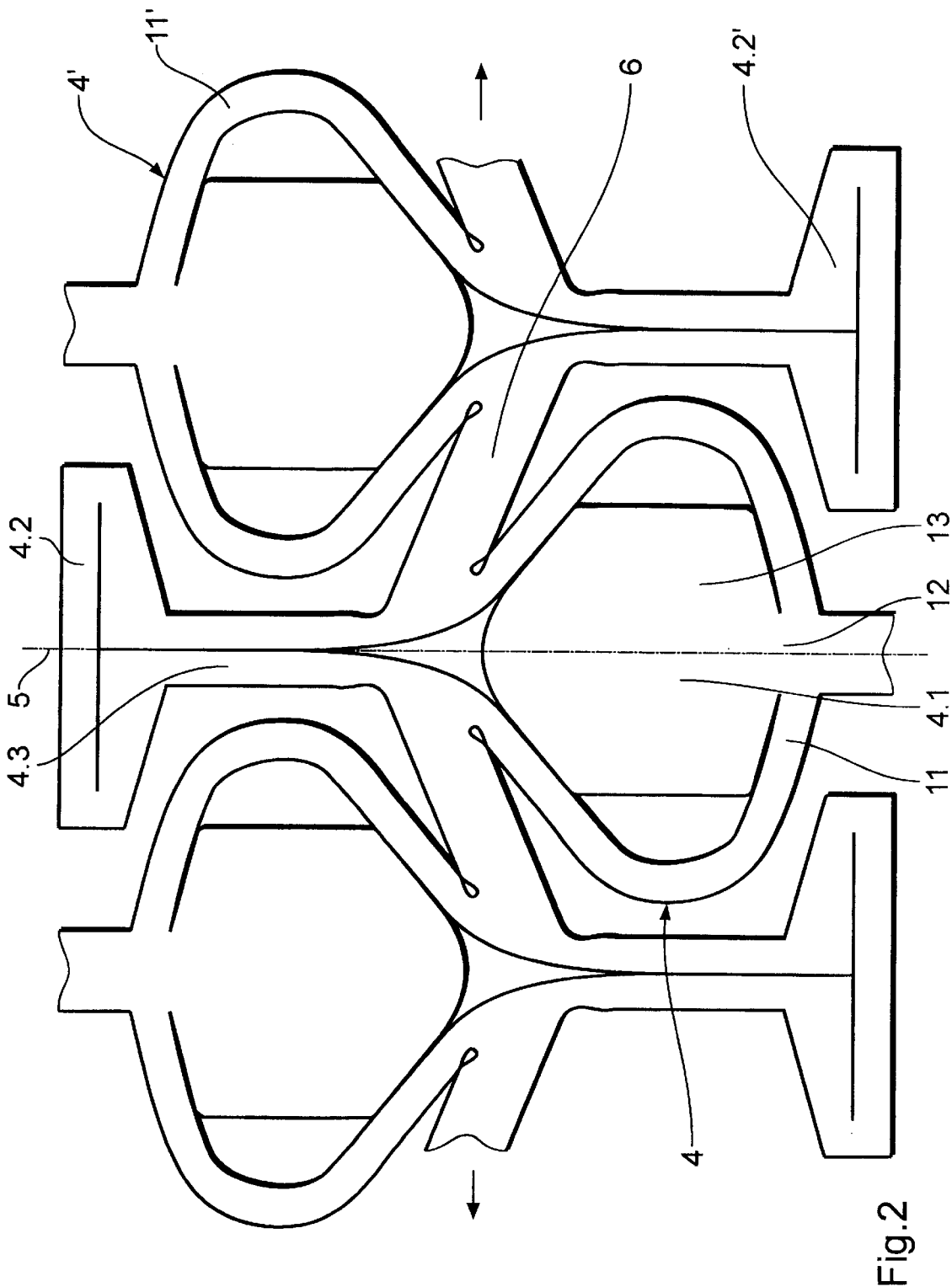
FIG. 2 is a larger-scale developed view of part of the surface according to FIG. 1 in partly expanded condition.

FIG. 2 shows a part of the surface 1 of the stent in the partly expanded condition. As the stent expands, the expandable elements 4, 4' move apart in the circumferential direction. The deformation forces are directed into the peripheral straps 11, 11' of the expandable elements 4, 4' via the joining strap 6 linking those elements. The angle of inclination of the joining strap 6 to the circumferential direction becomes smaller in the process, so that a bending moment is directed into the peripheral strap 11 in addition to a force in the circumferential direction. The effect of the bending moment is firstly that substantially the part of the peripheral strap 11 in the first section 4.1 is deformed. It first bulges greatly in the circumferential direction, thereby much shortening the first section 4.1. As a result of the marked shortening of the first section 4.1, the first section 4.1 of the first expandable element 4 and the second section 4.2' of the second expandable element 4' do not impede each other's expansion, although these two sections move towards each other in a longitudinal direction as the stent expands, due to the change of angle of the joining strap 6. This longitudinal movement is in turn responsible for avoiding shortening of the stent as it expands.

The piece 13 of the surface that is displaced in the direction of the intermediate section 4.3 in the deformation of the peripheral strap 11 assists in the even, gentle deformation of that strap.

Figure 3:
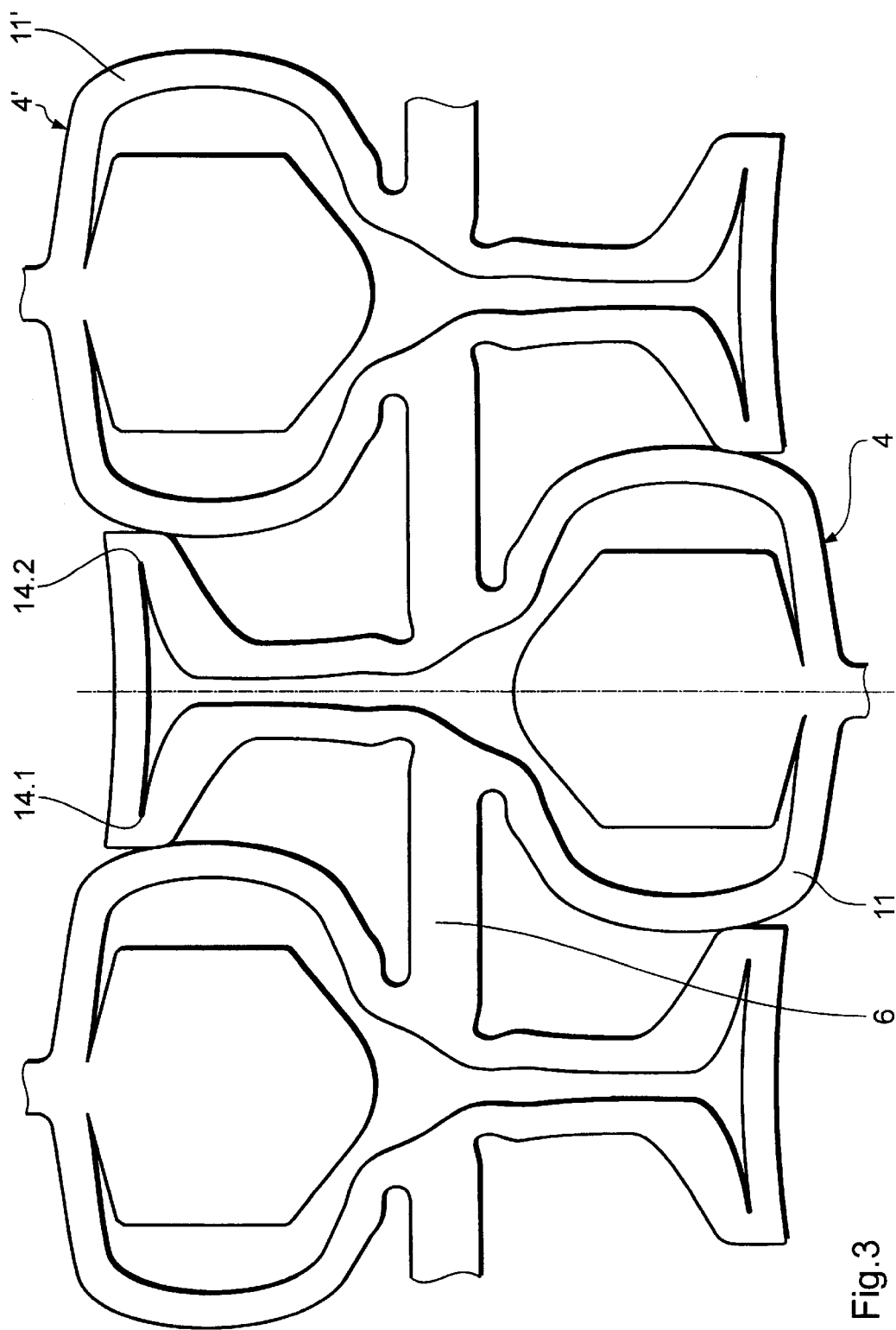
FIG. 3 is a developed view of the part of the surface according to FIG. 2, in a fully expanded condition.

FIG. 3 shows the part of the surface 1 from FIG. 2 in the fully expanded condition. The joining strap 6 now extends totally in the circumferential direction. The internal partition line 3.3 is opened relatively evenly over its whole extent, so that the deformation is similarly spread relatively evenly over the whole peripheral strap 11. No inadmissibly high tensions occur, especially at the end points 14.1 and 14.2 of the internal partition line 3.3 in the second section 4.2, which have particular notch sensitivity.

Figure 4:
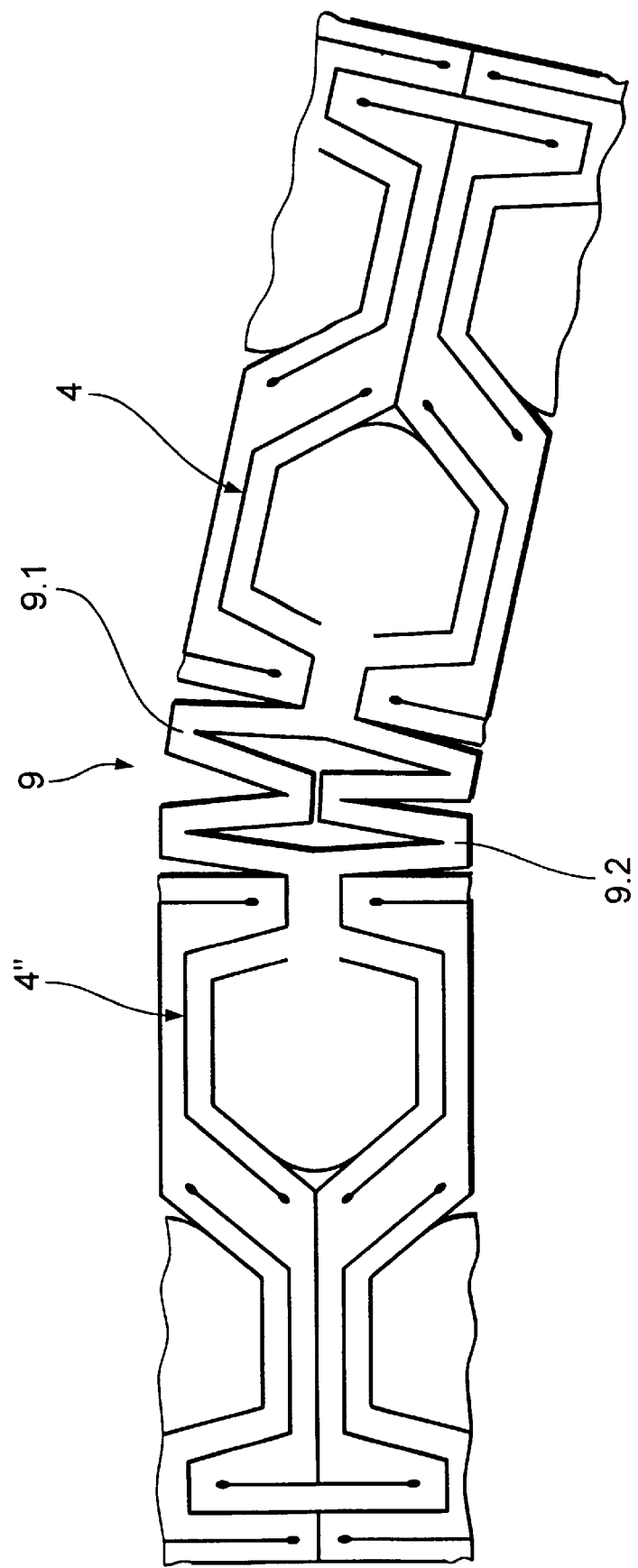
FIG. 4 shows a part of the surface according to FIG. 1 in the kinked, non-expanded condition of the stent.

FIG. 4 is a diagram showing the mode of operation of the stretching elements 9 when the whole stent is kinked in a plane parallel to that of the drawing, with the longitudinal axis of the stent located behind the plane of the drawing. The stretching straps 9.1 and 9.2 can first be drawn axially apart in the longitudinal direction of the stent. According to the buckling angle the strap 9.1 is then stretched still further while the strap 9.2 is compressed again. It is also possible, however, for the straps 9.1 and 9.2 merely to be stretched longitudinally to different degrees from the outset.

FIG. 5 shows the generated surface 1 from FIG. 1 in the non-expanded condition of the stent. The tubular body 2 has a closed surface 1 divided by partition lines 3 into expandable elements 4, joining straps 6 and attachments 8. The stretching elements 9 are arranged to form a closed annular region 15. The expandable elements 4 juxtaposed in the circumferential direction likewise form closed annular regions 16.1, 16.2.

Figure 6:
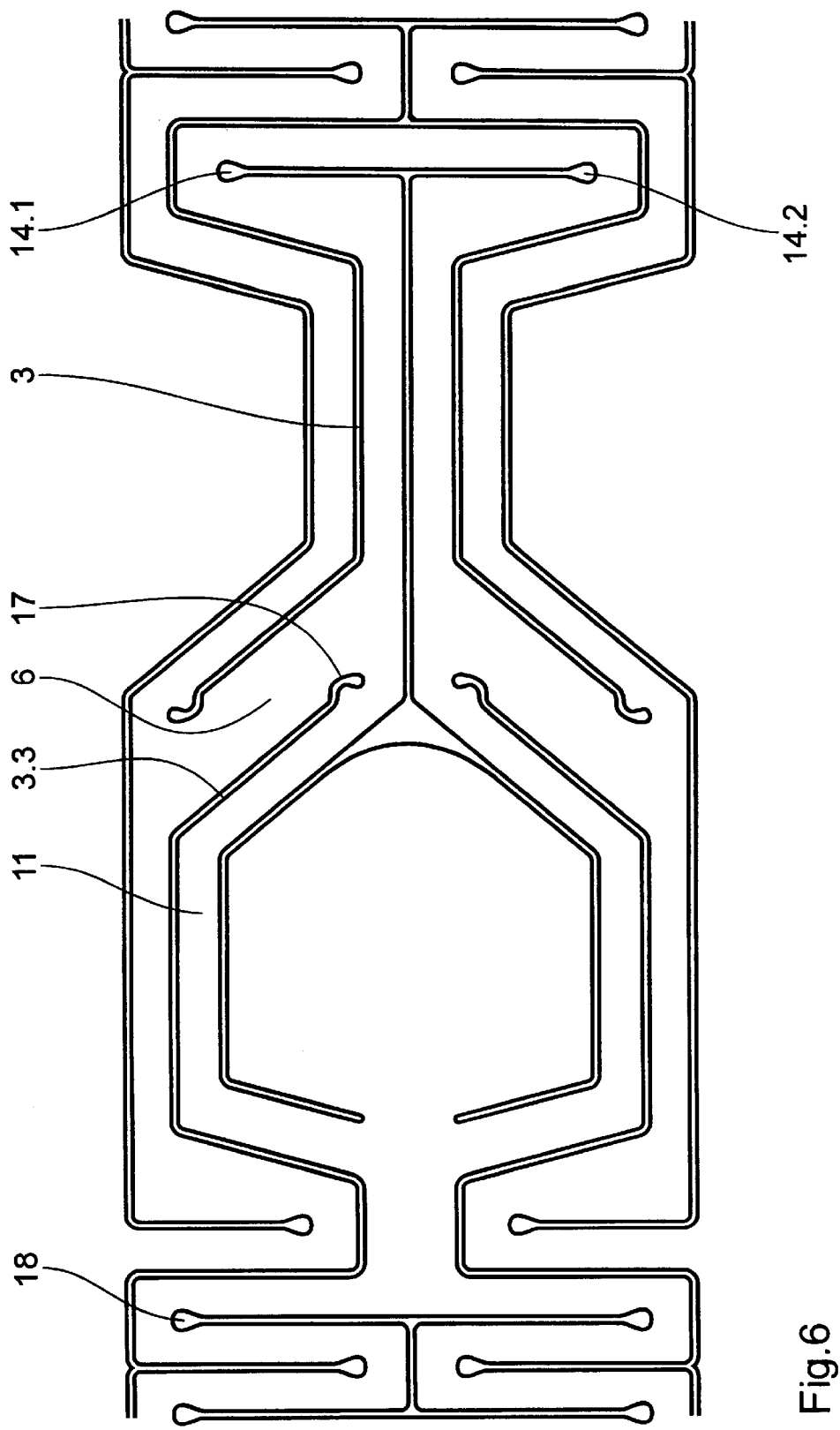
FIG. 6 is a larger-scale view of a part of the developed, non-expanded surface of another preferred embodiment of the stent according to the invention.

FIG. 6 shows a part of the surface of a further embodiment of the stent according to the invention, on a larger scale. The end points 14.1, 14.2, 17, 18 of all the partition lines 3 have widened and rounded portions, to reduce the notch tension sensitivity of the components in those positions. The drop shape was produced by reducing the advancing speed of the laser beam used to make the partition lines evenly to a standstill as it approached the end point of a partition line, so that the incision became wider and wider and was finally rounded off at the end point.

Figure 7:
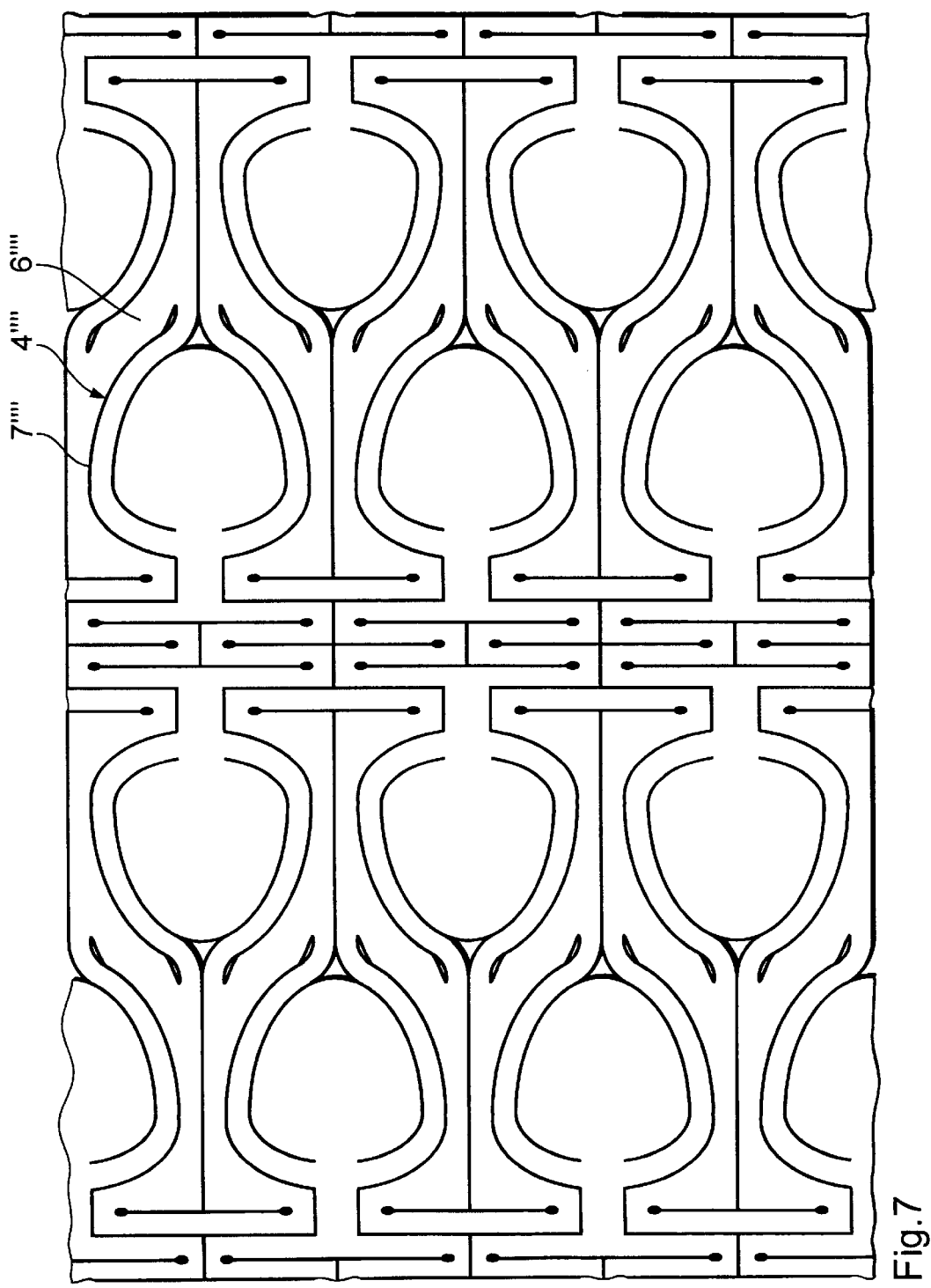
FIG. 7 is another preferred embodiment of the development of the surface of a non-expanded stent according to the invention.

FIG. 7 shows another preferred example of the development of the surface of a non-expanded stent according to the invention. In this embodiment the expandable elements 4"" and other components of the stent have substantially the same features and properties as in the embodiments described above. Only the external contour 7"" of the expandable elements 4"" differs, in having a very rounded shape, leading to further improvement in introduction of force and distribution of deformation through the expandable elements 4"".

The forms of the stent described above allow the tubular stent to expand without extreme notch tension values occurring at the joining points and causing strap regions to be damaged.

The stents illustrated here are made of tantalum, titanium or another biocompatible alloy of materials giving good tolerance by the body and excellent deformability. A microcoating of amorphous silicon carbide counteracts thrombus formation.

The form which the invention takes is not restricted to the preferred embodiments described above. A number of modifications, using the described solution even in fundamentally different structures, are beneficial.

I claim:

1. A stent comprising:
   at least one thin-walled, tubular body having a surface, the surface being divided into a plurality of strap-like, expandable elements each expandable element having at least one external contour and at least one end face wherein the expandable elements extend in a longitudinal direction of the stent and are expandable in a circumferential direction thereof;
   at least one joining strap linking at least two of the expandable elements juxtaposed in the circumferential direction of the stent;
   at least one end attachment linking at least one additional expandable element to an end face of an expandable element, the latter expandable element and the additional expandable element being positioned in the longitudinal direction of the stent,;
   wherein the surface in the non-expanded condition is substantially free of apertures and is divided by partition lines having considerably smaller widths compared with the strap widths of the expandable elements.

2. A stent according to claim 1, wherein the partition lines have a width that is substantially the width of a penetrating and separating incision when the surface of the tubular body is severed by means of a cutting beam.

3. A stent according to claim 2, wherein the partition lines have a width that is substantially the minimum obtainable width of a penetrating and separating incision when the surface of the tubular body is severed by means of a cutting beam.

4. A stent according to claim 1, wherein the at least one joining strap is inclined in both the longitudinal and the circumferential directions of the stent and are laterally defined, substantially over their whole length, by at least one partition line defining an external contour of a corresponding expandable element.

5. A stent according to claim 1, wherein the external contour of the expandable element is symmetrical with its longitudinal axis and has a flat first section extending in both the longitudinal and the circumferential directions, and a second section extending at least substantially in the circumferential direction, which sections are linked by an intermediate section extending substantially in the longitudinal direction.

6. A stent according to claim 5, wherein pairs of expandable elements adjoin each other in the circumferential direction of the stent, each pair having a first expandable element and a second expandable element which are turned 180° from each other, each expandable element having a first section and a second section where the first section of the first expandable element goes into a gap between the first section of the second expandable element and a second section of the second expandable element, and the joining strap is arranged between the first sections of the first and second expandable elements, and wherein the directly opposing external contours of the two expandable elements are bounded by the same partition lines.

7. A stent according to claim 1, wherein each expandable element has an internal partition line, running at a substantially constant distance from the external contour at least in sections, the internal partition line forming a narrow strap along the external contour inside the expandable element.

8. A stent according to claim 7, wherein the expandable element has an axis of symmetry, a first section, an intermediate section, and a second section, and the internal partition line runs at a substantially constant distance from the external contour in the first section of the expandable element, runs along the axis of symmetry in the intermediate section and is substantially T-shaped in the second section.

9. A stent according to claim 7, wherein the internal partition line in a first section of the expandable element has an interruption.

10. A stent according to claim 9, wherein the interruption of the internal partition line in the first section of the expandable element is located in the region of the end face of the first section.

11. A stent according to claim 1, wherein the expandable element has first and intermediate sections, and wherein the joining strap being positioned in a part of the intermediate section adjoining the first section is to link with the expandable element and being separated from the first section by partition line.

12. A stent according to claim 1, wherein at least one of the expandable elements has a first section, the end face being disposed on the first section so that the attachment is located at the end face of the first section.

13. A stent according to claim 11, wherein each expandable element has a first section with an end face, and the attachment comprises at least one stretching element, located between the end faces of the first sections of two expandable elements adjoining each other longitudinally of the stent, whereby the stretching element is comprised of at least two substantially parallel partition lines running in the circumferential direction of the stent, and has a form substantially in an S shape.

14. A stent according to claim 13, wherein, in the non-expanded condition of the stent, the stretching elements are positioned in the circumferential direction to form a closed annular region.

15. A stent according to claim 1, wherein pairs of expandable elements are located adjacent to each other in the circumferential direction of the stent and are connected by a joining strap having a center point and are point-symmetric with each other relative to the center point of the joining strap.

16. A stent according to claim 1, wherein the joining strap has an inclination to the circumferential direction of substantially 45° when the stent is not expanded.

17. A stent according to claim 1, wherein the joining strap is connected to the expandable elements at an angle of over 45° from the circumferential direction.

18. A stent according to claim 1, further comprising at least one peripheral strap wherein the expandable elements have a shape that substantially minimizes the total deformation which the peripheral strap undergoes on expansion.

19. A stent according to claim 1, further comprising a peripheral strap wherein the expandable elements have a shape such that an expansion of the tubular body causes deformation of the peripheral strap to be distributed over the length of the peripheral strap in such a way that the deformation does not exceed a predetermined value at any point along the peripheral strap.

20. A stent according to claim 1, further comprising a peripheral strap wherein any bending deformation allotted to a length of one-fifth of the peripheral strap is no greater than a quarter of a total bending deformation which the peripheral strap undergoes.

21. A stent according to claim 1, wherein joining regions between the expandable elements and the joining strap or the attachment are shaped so as to avoid any abrupt changes in the width of the joining strap.

22. A stent according to claim 1, further comprising a stretching strap and a plurality of deflection points for a force flux, and joining regions between the expandable element and the joining strap or the attachment, and wherein the deflection points are located on at least one of the expandable element and the stretching strap and are structured so that material tensions, including notch tension, do not exceed a predetermined value on deformation.

23. A stent according to claim 22, wherein the partition lines in the joining regions between the expandable element and the joining strap or the attachment, and at the deflection points have corresponding radii of curvature or a widened end region with a corresponding opening radius.

24. A stent according to claim 1, wherein the stent is made from one of titanium, tantalum, another biocompatible metal and a corresponding biocompatible metal alloy.

25. A stent according to claim 24, further comprising a coating of amorphous silicon carbide.

26. A method of making a stent according to claim 1, wherein the partition lines in the surface of the tubular body are produced by at least one cutting beam directed onto the surface of the tubular body.

27. A method according to claim 26, wherein a laser beam is used as the cutting beam.

28. A method according to claim 26 of making a stent having partition lines with widened end regions wherein the cutting beam as it travels between the widened end regions of the partition lines has a speed component exclusively along the partition lines.

29. A method according to claim 26, wherein the cutting beam has a a maximum advancing speed T which a clean incision is still obtained in the surface and the cutting beam is advanced substantially at the maximum advancing speed.

30. A method according to claim 26 of making a stent having partition lines with widened end regions wherein the cutting beam intermittently has a speed component across the partition lines to produce the widened end regions.

31. A method according to claim 30, wherein the cutting beam makes an advancing movement in a meander-shaped and/or circular or elliptical pattern.

32. A method according to claim 26 of making a stent having partition lines with widened end regions wherein the cutting beam has an advancing speed and the widened end regions of the partition lines are produced by reducing the advancing speed of the cutting beam in the vicinity of the widened end regions.

33. A method according to claim 32 of making a stent having partition lines with widened end regions wherein the widened end regions of the partition lines are produced by holding the cutting beam still in the appropriate cutting position.

\* \* \* \* \*